United States Patent [19]

Mulligan et al.

[11] Patent Number: 5,460,959
[45] Date of Patent: Oct. 24, 1995

[54] TRANSDUCED FIBROBLASTS

[75] Inventors: Richard C. Mulligan, Cambridge; James M. Wilson, Waltham, both of Mass.

[73] Assignee: Whitehead Institute for Biomedical Research, Cambridge, Mass.

[21] Appl. No.: 70,646

[22] Filed: Jun. 1, 1993

Related U.S. Application Data

[63] Continuation of Ser. No. 96,074, Sep. 11, 1987, abandoned.
[51] Int. Cl.$^6$ .............................. C12N 5/10; C12N 15/86
[52] U.S. Cl. ..................... 435/172.3; 424/93.21; 435/69.1; 435/240.1; 435/240.2; 435/240.23; 435/240.24; 435/320.1; 935/32; 935/34; 935/57; 935/62; 935/70; 935/71
[58] Field of Search .................... 435/240.1, 240.2, 435/240.23, 320.1, 240.24; 424/93.1, 93.2, 93.21

[56] References Cited

U.S. PATENT DOCUMENTS

| | | | |
|---|---|---|---|
| 4,634,665 | 1/1987 | Axel et al. | 435/172.3 X |
| 4,861,719 | 8/1989 | Miller | 435/236 |
| 4,868,116 | 9/1989 | Morgan et al. | 435/240.2 |
| 5,219,740 | 6/1993 | Miller et al. | 435/69.6 |
| 5,399,346 | 3/1995 | Anderson et al. | 424/93.21 |

FOREIGN PATENT DOCUMENTS

| | | |
|---|---|---|
| 0178220 | 4/1986 | European Pat. Off. . |

OTHER PUBLICATIONS

H. Temin, in *Gene Transfer*, R. Kucherlapati, ED., Plenum Press, N.Y., (1986), pp. 149–187.
J. G. Hellerman et al (1984) Proc. Natl. Acad. Sci. USA 81: 5340–5344.
A. A. Demetriou et al (1986) Science 233: 1190–1192.
K. O'Hare et al. (1981) Proc. Natl Acad Sci USA 78(3): 1527–1531.
American Type Culture Collection Catalogue of Cell Lines and Hybridomas, 5th Edition, pp. 154–157 (1985).
R. A. Fleischman (1991) The American Journal of the Medical Sciences 301(5): 353–363.
Garver, R. I., et al., Science 237: 762–764 (1987).
Selden, R. F., et al., Sciene 236: 714–718 (1987).
Hendy, G. N., et al., Proc. Natl. Acad. Sci. 78: 7365–7369 (1981).
Cone, R. D., et al., Proc. Natl. Acad. Sci. 81: 6349–6353 (1984).
Palmer, T. D., et al., Proc. Natl. Acad. Sci. 84: 1055–1059 (1987).
Sorge, J., et al., Proc. Natl. Acad. Sci. 84: 906–909 (1987).
Sherry Hwang, L. H., et al., J. Virol. 150(2): 417–424 (1984).
Doehmer, J. et al., Proc. Natl. Acad. Sci. 79: 2268–72 (1982).
Lugo, T. G., et al., Molec. Cell. Biol. 7(8): 2814–2820 (1987).
Seliger, B., et al, J. Virol. 61(8) 2567–72 (1987).
Miller, A. D. et al., Abstract of Paper from Cold Spring Harbor Symposia on Quantitative Biology, Cold Spring Harbor Laboratory, (1986).
Choudary, P. V. et al., DNA 5: 78 (1986).
Choudary, et al., Mol. Biol. Med. 3: 293–299 (1986).
Choudary, et al., Fed. Proc. 45: 1616 (1986).
Choudary, et al., Cold Spring Harbor Symposia on Quantitative Biology LI:1047–1052 (1986).
Choudary, et al., DNA Congress Abstracts 5:54–56, 71, 78 (1986).
Gazit, et al., J. Virol 60: 19–28 (1986).
Stratowa, et al., EMBO J. 1: 1573–1578 (1982).
American Type Culture Collection Catalog of Strains II, 4th ED p. 68 (1983).
Sher, et al., Transplantation 36: 552–557 (1983).
Miller et al., Mol. Cell Bio. 6: 2895–2902 (1986).
Smets, L. A., In *Genetic Origins of Tumor Cells* pp. 1–10 Cleton and Simon Editors, Martinus Nighoff Publishers (1980).
Tani, K., et al. Blood 74: 1274–1280 (1980).
Axelrod, J. H., et al. Proc. Natl. Acad. Sci. 87: 5173–5177 (1990).
Fischer, L. J., et al. Neuron 6: 371–380 (1991).
Palmer, T. D., et al. Proc. Natl. Acad. Sci. 88:1330–1334 (1991).
Scharfman, R., et al. Proc. Natl. Acad. Sci. 88:4626–4630 (1991).
St. Louis, D. et al. Proc. Natl. Acad. Sci. 85: 3150–3154 (1988).
Demetriou et al. Proc. Natl. Acad. Sci. 83: 7475–7479 (1986).

*Primary Examiner*—Jacqueline M. Stone
*Assistant Examiner*—Johnny F. Railey, II
*Attorney, Agent, or Firm*—Albert P. Halluin; Pennie & Edmonds

[57] ABSTRACT

Fibroblasts transduced with genetic material encoding a polypeptide or protein of interest and, optionally, a selectable marker, as well as methods for making and using the transduced fibroblasts. Such fibroblasts are useful in delivering the encoded polypeptide or protein, such as an enzyme, a hormone or a drug, to an individual who has had a graft or implant of the transduced cells.

17 Claims, 4 Drawing Sheets

VECTORS WITH SELECTABLE MARKERS

*Fig 2a*  pZIPNeo (SVX)

*Fig 2b*  pLJ

*Fig 2c*  pWe

PRO = β-Actin
Histone
Thymidine kinase
Thy-1
Albumin

VECTORS WITHOUT SELECTABLE MARKERS

*Fig 2d*  pEm

*Fig 2e*  pIp

PRO = β-Actin
Histone
Thymidine kinase
Thy-1
Albumin

TRANSDUCED FIBROBLASTS

This is a continuation of application Ser. No. 07/096,074 filed on Sep. 11, 1987 and now abandoned.

DESCRIPTION

1. Sponsorship

Work described herein was supported by grants from the National Institutes of Health and the Howard Hughes Medical Institute.

2. Background

In the embryo, the mesoderm is the middle of the three primary third germ layers, and lies between the ectoderm and the endoderm. It gives rise, during development, to the connective tissues, all body musculature, blood, cardiovascular and lymphatic systems, most of the urogenital system and the lining of the pericardial, pleural and peritoneal cavities. That portion of the mesoderm which produces the connective tissue, blood vessels and blood, the lymphatic system and the heart is referred to as the mesenchyme. One type of cells produced by mesenchymal cells is fibroblast cells, which are stellate or spindle-shaped cells with cytoplasmic processes. They are present in connective tissue and are capable of forming collagen fibers.

Fibroblasts, like other cells in the body, contain an entire complement of all genetic material. However, only a small percentage of the genes they contain are expressed at biologically functional levels. That is, most of the genes in fibroblasts are not expressed at all, or are expressed at such low levels that the polypeptides they encode are produced in undetectable amounts or concentrations which are biologically nonfunctional or insignificant.

It is possible, using methods developed in recent years, to attain interspecies genetic recombination. Genes derived from different biological classes are able to replicate and be expressed in a selected microorganism. Therefore, it is possible to introduce into a microorganism genes specifying a metabolic or synthetic function (e.g., hormone synthesis, protein synthesis, nitrogen fixation) which is characteristic of other classes of organisms by linking the genes to a particular viral or plasmid replicon.

Since the late 1970s, progress has been made toward the development of general methods for introducing cloned DNA sequences into mammalian cells. At the present time, however, there is a need for an effective method of stably introducing genetic material into fibroblasts and enabling them to express genetic material which they do not normally express, or normally express at biologically insignificant levels.

SUMMARY OF THE INVENTION

The invention described herein relates to genetically engineered mesenchymal or connective tissue cells and particularly to genetically engineered fibroblasts which express in biologically significant concentrations genetic material which is not normally expressed in significant concentrations in such cells. It also relates to methods of stably introducing into fibroblasts such genetic material and methods of using the genetically engineered fibroblasts.

Fibroblasts of this invention have stably incorporated in them genetic material of interest and express the incorporated genetic material. This genetic material of interest is referred to herein as incorporated genetic material. The incorporated genetic material can be DNA or RNA which does not normally occur in fibroblasts; DNA or RNA which normally occurs in fibroblasts but is not expressed in them at levels which are biologically significant (i.e., levels sufficient to produce the normal physiological effects of the polypeptide it encodes); DNA or RNA which occurs in fibroblasts and has been modified so that it is expressed in fibroblasts; and any DNA or RNA which can be modified to be expressed in fibroblasts, alone or in any combination thereof. The incorporated genetic material expressed by fibroblasts of the present invention can include genetic material encoding a selectable marker, thus providing a means by which cells expressing the incorporated genetic material are identified and selected for. Fibroblasts containing incorporated genetic material are referred to as transduced fibroblasts.

In particular, retroviral vectors have been used to stably transduce fibroblasts with genetic material which includes genetic material encoding a polypeptide or protein of interest not normally expressed at biologically significant levels in fibroblasts. The genetic material introduced in this manner also included genetic material encoding a dominant selectable marker. Genetic material including DNA encoding a polypeptide of interest and DNA encoding a dominant selectable marker has been introduced into cultured fibroblasts. Expression of these genes by the fibroblasts into which they have been incorporated (i.e., fibroblasts transduced by the use of retroviral vectors) has also been demonstrated.

A method of transplanting transduced fibroblasts which express the incorporated genetic material they contain is also a subject of the present invention. Transduced fibroblasts of the present invention are used for the constitutive delivery of polypeptides or proteins, useful in prevention and therapy or treatment, which are presently administered parenterally. They can be used in skin grafts and in glial cell or fibroblast implants which introduce DNA encoding a polypeptide or protein of interest into the central nervous system.

There are many advantages to fibroblasts of the present invention and the delivery system for a polypeptide or protein of interest which make them very useful. For example, a skin graft using fibroblasts which include incorporated genetic material encoding a polypeptide of interest (e.g., a hormone, enzyme, drug) synthesizes the encoded polypeptide and thus serves as a continuous delivery system for that polypeptide. In this way, the hormone or other polypeptide is diffused into the bloodstream of the individual receiving the skin graft.

An important advantage is that the genetically engineered fibroblasts of the present invention can be used to administer therapeutic proteins (e.g., hormones, enzymes, clotting factors) which are presently administered intravenously, intramuscularly or subcutaneously. In addition, there is no need for extensive (and often costly) purification of the polypeptide before it is administered to an individual, as is generally necessary with an isolated polypeptide (e.g., insulin). Fibroblasts modified according to the present invention produce the polypeptide hormone as it would normally be produced. In the case of insulin, for example, the genetically engineered fibroblasts produce insulin in the same form as that made in the pancreas.

Another advantage to the use of a graft having fibroblasts of the present invention is that by controlling the size of the graft, the amount of the polypeptide delivered to the body can be controlled. In addition, in the case of a skin graft, it can be excised if there is no longer a need for the polypeptide being produced. For example, if delivery of the polypeptide (hormone, enzyme, or drug) is necessary only for a specific period, the engineered graft can be removed when treatment is no longer needed.

Another important advantage of the delivery system of this invention is that because it is a continuous delivery system, the fact that polypeptide hormones have very short half lives is not a limitation. For example, the half life of human growth hormone (HGH) is approximately 19 minutes, of parathyroid hormone, approximately 2½ to 5 minutes and, of native insulin (pure insulin), approximately 3 to 4 minutes.

Because genes can be introduced into fibroblasts using a retroviral vector, they can be "on" (subject to (the retroviral vector control); in such a case, the gene of interest is transcribed from a retroviral promoter. A promoter is a specific nucleotide sequence recognized by RNA polymerase molecules that start RNA synthesis. Alternatively, retroviral vectors having additional promoter elements (in addition to the promoter incorporated in the recombinant retrovirus) which are responsible for the transcription of the genetic material of interest, can be used. For example, a construct in which there is an additional promoter modulated by an external factor or cue can be used, making it possible to control the level of polypeptide being produced by the fibroblasts by activating that external factor or cue. For example, heat shock proteins are proteins encoded by genes in which the promoter is regulated by temperature. The promoter of the gene which encodes the metal-containing protein metallothionine is responsive to cadmium ($Cd^{++}$) ions. Incorporation of this promoter or another promoter influenced by external cues also makes it possible to regulate the production of the polypeptide by the engineered fibroblasts.

BRIEF DESCRIPTION OF THE DRAWINGS

FIG. 2, parts a–e, is a schematic representation of retroviral vectors, each having a recombinant genome, useful in the present invention.

DETAILED DESCRIPTION OF THE INVENTION

Genetic material of interest has been incorporated into fibroblasts and expressed in the resulting genetically engineered fibroblasts. Genetic material incorporated into fibroblasts according to the method described can be DNA or RNA which does not normally occur in fibroblasts; DNA or RNA which normally occurs in fibroblasts but is not expressed in them at levels which are biologically significant (levels sufficient to produce the normal physiological effects of the polypeptide it encodes); DNA or RNA which occurs in fibroblasts and has been modified so that it is expressed in such cells; and any DNA or RNA which can be modified to be expressed in fibroblasts, alone or in any combination thereof. This genetic material of interest is referred to herein as incorporated genetic material. Fibroblasts of the present invention express the incorporated genetic material. The incorporated genetic material (i.e., DNA or RNA) expressed by fibroblasts of the present invention is genetic material encoding a polypeptide or a protein of interest (genetic material of interest), alone or in combination with a gene encoding a selectable marker.

For example, genetic material encoding a hormone has been introduced into fibroblasts by exposing them to media that contains a virus having a recombinant genome (i.e., by infecting them). The media used is obtained by harvesting media in which producer cells (e.g., a Psi am or amphotropic producer) have been grown. That is, producer cells have been grown in tissue culture to a confluent density in Dulbecco's Modified Eagle's medium (DME) with 10% calf serum (CS) and penicillin and streptomycin. Fresh media is added and subsequently (e.g., approximately 12 hours later), the media is harvested. Approximately 10 ml of media is harvested from a 10 cm plate of confluent producer cells. The spent media (or viral stock) is filtered through a 0.45 micron Millipore filter to remove detached producer cells and is used immediately to infect cells or is stored at −70° C. Media is removed from a subconfluent plate of fibroblasts (recipient fibroblasts) and quickly replaced with viral stock (e.g., 5 ml/10 cm. plate) containing 8 mg/ml. of Polybrene (Aldrich). Subsequently (e.g., approximately 12 hours later), this is removed and replaced with fresh media. Thus, the media used is a viral supernatant. The recombinant genome of the infectious virus includes the genetic material of interest. The recombinant genome can also have genetic material encoding a dominant selectable marker.

Thus, fibroblasts are made which express a polypeptide not normally expressed by such cells at biologically significant levels and, optionally, a dominant selectable marker.

In particular, fibroblasts are exposed to media containing infectious virus produced in Psi am cells; the infectious virus contain a recombinant genome having the genetic material of interest. The recombinant genome in one instance includes genetic material encoding human parathyroid hormone (hPTH). Optionally, it can also include a gene encoding a dominant selectable marker (e.g., the neo gene which encodes neomycin resistance). As a result, the fibroblasts are transduced—that is, the genetic material of interest (in this case, DNA encoding hPTH and, optionally, the neo gene) is stably introduced into the fibroblasts. The transduced fibroblasts express the encoded hPTH and, if the neo gene is present, express it, resulting in cells having the selectable trait.

Alternatively, fibroblasts are transduced as a result of exposure to media containing infectious virus in which the recombinant genome includes DNA encoding one or more of the following:

the receptor for low density lipoproteins;

human growth hormone;

the gene that confers resistance to histidonal;

human adenosine deaminase;

the receptor for interleukin 2;

human beta-globin;

human alpha-globin;

a mutant form of dihydrofolate reductase;

multidrug resistance;

glucose cerebrosidase from humans;

the E1A gene from adenovirus;

many different genes for HLA in humans;

human albumin;

human ornithine transcarbamalyase beta-galactosidase from *E. coli;* resistance to neomycin in *E. coli;* human insulin; and the envelope protein from Moloney murine leukemia virus.

Fibroblasts expressing the incorporated genetic material are grown to confluence in tissue culture vessels; removed from the culture vessel in which they were grown; and introduced into or applied to the body. They have been introduced into the intraperitoneal cavity, both alone and coated onto microcarrier beads (approximately 100 cells/bead) having collagen-covered surfaces. Alternatively, they can be applied as a component of a skin graft, using a method such as that described by Bell in U.S. Pat. No. 4,485,096, the teachings of which are incorporated herein by reference.

Fibroblasts expressing the incorporated genetic material can also be introduced into the central nervous system. This can be done, for example, by introducing genetically engineered fibroblasts of the present invention (i.e., fibroblasts into which a gene of interest has been introduced) directly into specific regions of the brain through stereotactic administration. It can also be introduced into the cerebrospinal fluid via lumbar puncture or directly into the ventricles, which would result in seeding of the fibroblasts along the meninges.

Once introduced into or applied to the body, the transduced fibroblasts provide a continuous supply of the hormone, enzyme or drug encoded by the genetic material of interest. In the example described, the encoded product is hPTH.

The amount of the hormone, enzyme or drug supplied in this way can be modified or regulated as needed. This is done, for example, by using external cues or factors which affect their production; by controlling the size of the graft applied or the quantity of fibroblasts introduced into the body; or by removing the graft.

Cultured Fibroblasts

Fibroblasts are obtained from a subject by skin biopsy (e.g., a small punch biopsy from any area of the body). The resulting tissue is placed in tissue culture media and separated into small pieces (e.g., by use of scalpels to tease apart the tissue). Small chunks of the tissue are placed on a wet surface of a tissue culture flask; approximately 10 pieces are placed in each flask. The flask is turned upside-down, closed tight and left at room temperature overnight. After 24 hours at room temperature, the flask is inverted; the chunks of tissue remain fixed to the bottom of the flask and fresh media (e.g., Ham's F12 media with 10% FBS and penicillin and streptomycin) is added. This is then incubated at 37° for approximately one week. At this time, fresh media is added and subsequently changed every several days. After an additional two weeks in culture, a monolayer of fibroblasts emerges. The monolayer is trypsinized and scaled up into larger flasks. The fibroblasts can be maintained in culture for approximately 50 generations; at approximately that time, they undergo what is called a crisis and subsequently do not grow very well. Soon after the fibroblasts are scaled up to (replated onto) larger flasks, they are infected according to the protocol described below.

Retroviral Vectors

Figure 1:
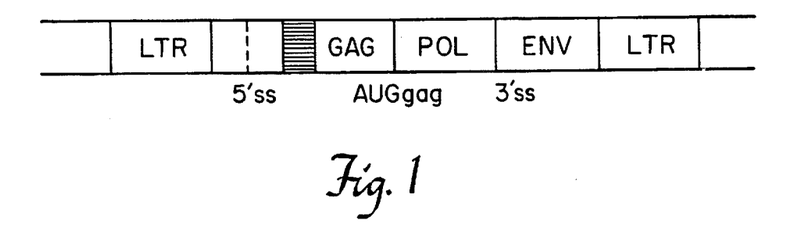
FIG. 1 is a schematic representation of a wild type murine leukemia virus (retroviral) genome.

Retroviruses are RNA viruses; that is, the viral genome is RNA. This genomic RNA is, however, reverse transcribed into a DNA intermediate which is integrated very efficiently into the chromosomal DNA of infected cells. This integrated DNA intermediate is referred to as a provirus. As shown in FIG. 1, the retroviral genome and the proviral DNA have three genes: the gag, the pol and the env, which are flanked by two long terminal repeat (LTR) sequences. The gag gene encodes the internal structural (nucleocapsid) proteins; the pol gene encodes the RNA-directed DNA polymerase (reverse transcriptase); and the env gene encodes viral envelope glycoproteins. The 5' and 3' LTRs serve to promote transcription and polyadenylation of virion RNAs.

Adjacent to the 5' LTR are sequences necessary for reverse transcription of the genome (the tRNA primer binding site) and for efficient encapsidation of viral RNA into particles (the Psi site). Mulligan, R.C., *In: Experimental Manipulation of Gene Expression*, M. Inouye (ed), 155–173 (1983); Mann, R., et al., *Cell*, 33:153–159 (1983); Cone, R.D. and R.C. Mulligan, *Proceedings of the National Academy of Sciences*, U.S.A., 81:6349–6353 (1984).

If the sequences necessary for encapsidation (or packaging of retroviral RNA into infectious virions) are missing from the viral genome, the result is a cis defect which prevents encapsidation of genomic RNA. However, the resulting mutant is still capable of directing the synthesis of all virion proteins. Mulligan and co-workers have described retroviral genomes from which these Psi sequences have been deleted, as well as cell lines containing the mutant stably integrated into the chromosome. Mulligan, R.C., *In: Experimental Manipulation of Gene Expression*, M. Inouye (ed), 155–173 (1983); Mann, R., et al., *Cell*, 33:153–159 (1983); Cone, R.D. and R.C. Mulligan, *Proceedings of the National Academy of Sciences*, U.S.A., 81:6349–6353 (1984). The teachings of these publications are incorporated herein by reference.

The Psi 2 cell line described by Mulligan and co-workers was created by transfecting NIH 3T3 fibroblasts with pMOV-Psi⁻, which is an ecotropic Moloney murine leukemia virus (Mo-MuLV) clone. pMOV-Psi⁻ expresses all the viral gene products but lacks the Psi sequence, which is necessary for encapsidation of the viral genome. pMOV-Psi⁻ expresses an ecotropic viral envelope glycoprotein which recognizes a receptor present only on mouse (and closely related rodent) cells.

Another cell line is the Psi am line, which are Psi-2-like packaging cell lines. These Psi-am cell lines contain a modified pMOV-Psi-genome, in which the ecotropic envelope glycoprotein has been replaced with envelope sequences derived from the amphotropic virus 4070A. Hartley, J.W. and W.P. Rowe, *Journal of Virology*, 19:19–25 (1976). As a result, they are useful for production of recombinant virus with amphotropic host range. The retrovirus used to make the Psi am cell line has a very broad mammalian host range (an amphotropic host range) and can be used to infect human cells. If the recombinant genome has the Psi packaging sequence, the Psi-am cell line is capable of packaging recombinant retroviral genomes into infectious retroviral particles. Cone, R. and Mulligan, R., *Proceedings of the National Academy of Sciences*, USA, 81:6349–6353 (1984).

The retroviral genome has been modified by Cone and Mulligan for use as a vector capable of introducing new genes into cells. As shown in FIG. 2, the gag, the pol and the env genes have all been removed and a DNA segment encoding the neo gene has been inserted in their place. The neo gene serves as a dominant selectable marker. The retroviral sequence which remains part of the recombinant genome includes the LTRs, the tRNA binding site and the Psi packaging site. Cepko, C. et al., *Cell*, 37:1053–1062 (1984).

Additional vector constructions which have been used in producing transduced fibroblasts of the present invention are represented in FIG. 2 and are described in detail below.

pZip. The construction of this vector has been described in Cepko, C.L. et al. *Cell* 37:1053 (1984). Briefly, this vector is capable of expressing two genes: the gene of interest and the Neogene as a selectable marker.

The gene of interest is cloned into a BamHI site just distal to the 5' LTR, flanked by a splice donor site, and a splice acceptor site. Two transcipts will result from transcription of the provirus: the unprocessed transcript will result in expression of the gene of interest while the "processed" transcript will result in expression of the Neogene.

pLJ. The characteristics of this vector have been described in Korman, A.J. et al., *Proceedings of the National Academy of Sciences*, USA 84:2150 (1987). This vector is capable of expressing two genes: the gene of interest and a dominant selectable marker, such as the Neogene. The gene of interest is cloned in direct orientation into a BamHI/SmaI/SalI cloning site just distal to the 5' LTR, while, the Neogene is placed distal to an internal promoter (from SV40) which is farther 3' than is the cloning site (is located 3' of the cloning site). Transcription from PLJ is initiated at two sites: 1) the 5' LTR, which is responsible for expression of the gene of interest and 2) the internal SV40 promoter, which is responsible for expression of the Neogene.

pWe. The construction and initial characterization of this vector have been described. Choudory, P.V. et al, CSH Symposia *Quantitative Biology*, L.I. 1047 (1986). Briefly, this vector can drive expression of two genes: a dominant selectable marker, such as Neo, which is just downstream from the 5' LTR and a gene of interest which can be cloned into a BamHI site just downstream from an internal promoter capable of high level constitutive expression. Several different internal promoters, such as the beta-actin promoter from chicken (Choudory, P.V. et al, CSH Symposia *Quantitative Biology*, L.I. 1047 (1986)), and the histone H4 promoter from human (Hanly, S.M. et al., *Molecular and Cellular Biology* 5:380 (1985)) have been used. Expression of the Neogene is from a transcript initiated at the 5' LTR; expression of the gene of interest is from a transcript initiated at the internal promoter.

pEm. In this simple vector, the entire coding sequence for gag, pol and env of the wild type virus is replaced with the gene of interest, which is the only gene expressed. The components of the pEm vector are described below. The 5' flanking sequence, 5' LTR and 400 bp of contiguous sequence (up to the BAMHI site) is from pZIP. The 3' flanking sequence and LTR are also from pZIP; however, the Cla site 150 bp upstream from the 3' LTR has been linkered with BamHI and forms the other half of the BamHI cloning site present in the vector. The HindIII/EcoR1 fragment of pBR322 forms the plasmid backbone. This vector is derived from sequences cloned from a strain of Moloney Murine Leukemia virus. An analogous vector has been constructed from sequences derived from the myeloproliferative sarcoma virus.

pIp. This vector is capable of expressing a single gene driven from an internal promoter. The construction of these vectors is summarized below. The 5' section of the vector, including the 5' flanking sequences, 5' LTR, and 1400 bp of contiguous sequence (up to the xho site in the gag region) is derived from wild type Moloney Leukemia virus sequence. Shinnick et al., *Nature*, 293:543 (1981). The difference between the two is that a SacII linker is cloned into an HaeIII restriction site immediately adjacent to the ATG of the gag gene. The 3' section of the vector, including the 3' flanking sequences, 3' LTR and 3' contiguous sequence (up to the ClaI site in the env coding region) is from pZIP. However, there are two modifications: 1) the ClaI site has been linked to BamHI and 2) a small sequence in the 3' LTR spanning the enhancer (from PvuII to XbaI) has been deleted. Bridging the 5' and 3' sections of the vector is one of several promoters; each one is contained on a XhoI/BamHI fragment, and each is capable of high level constitutive expression in most tissues. These promoters include beta-actin from chicken (Choudory, P.V. et al, CSH Symposia *Quantitative Biology*, L.I. 1047 (1986), and thymidine Kinase from Herpes Simplex Virus, histone H4 from human (Hanly, S.M. et al., *Molecular and Cellular Biology* 5:380 (1985)). The vector backbone is the HindIII/EcoRI fragment from pBR322. The gene of interest is cloned into the BamHI site in direct orientation, just downstream from the internal promoter.

ROvectors. This category represents a heterogeneous group of vectors in which the gene of interest contains all the sequences necessary for transcription (i.e., promoter/enhancer, coding sequence with and without introns, and poly adenylation signal) and is introduced into the retroviral vector in an orientation in which its transcription is in a direction opposite to that of normal retroviral transcription. This makes it possible to include more of the cis-acting elements involved in the regulation of the introduced gene. Virtually, any of the above described genes can be adapted to be a RO vector. One example is described by Cone et al. in which the entire beta globin gene was cloned in reverse orientation into the BamHI site of pZip. Cone, R. and R.C. Mulligan *Proceeding of the National Academy of Sciences*, U.S.A., 81:6349–6353 (1984). RO vectors have been constructed in which the gene of interest has been cloned into the XhoI/BamHI site of pip (essentially replacing the internal promoter).

Vectors into which a gene of interest has been inserted are shown in Table 1 as well as results obtained when the construction was tested for expression.

TABLE 1

Vectors Containing Gene of Interest

| Protein of Function | Vector | | | | | |
|---|---|---|---|---|---|---|
| | pZip | pLJ | pWe | pEm | pIP | pRO |
| Human growth homone | 3 | 3 | | | | 3 |
| Human PTH | 3 | 3 | | 3 | 3 | |
| Human receptor for LDL | | | | 3 | 3 | |
| Human albumin | | 3 | 2 | | | 1 |
| Human ornithine transcarbamlyase | | | | 1 | 1 | |
| Human adenosine | | | | | 3 | |

TABLE 1-continued

Vectors Containing Gene of Interest

| Protein of Function | pZip | pLJ | pWe | pEm | pIP | pRO |
|---|---|---|---|---|---|---|
| deaminase | | | | | | |
| Receptor for interleukin-2 | | | 3 | 3 | | |
| Human Beta globin | | | | | | 3 |
| Human alpha globin | | | | | | 3 |
| Mutant dihydrofolate reductase | 3 | | | 3 | 3 | |
| Multidrug resistance | | | | | 3 | |
| Human glucose cerebrosidase | | | 3 | | | |
| Neomycin | 3 | 3 | 3 | 3 | 3 | |
| EIA gene from aderovirus | 3 | | | | | |
| Histidinol$^R$ from E. coli | 3 | | | | | |
| -galactosidase from E. coli | | 3 | | | | |
| HLA antigens from human | | 3 | | | | |
| Human insulin | | 3 | | | | |
| Envelope from Moloney MLV | 1 | | 3 | | | |

Figure 2A:
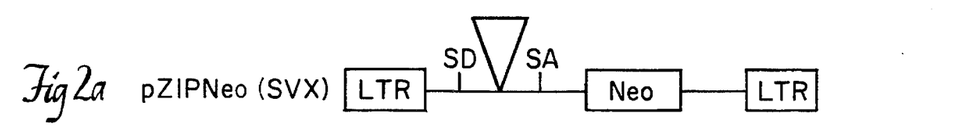
FIG. 2a is pZIPNeo.
Figure 2B:
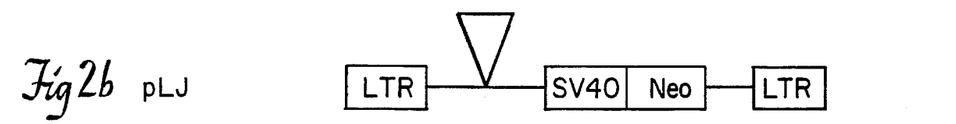
FIG. 2b is pLJ.
Figure 2C:
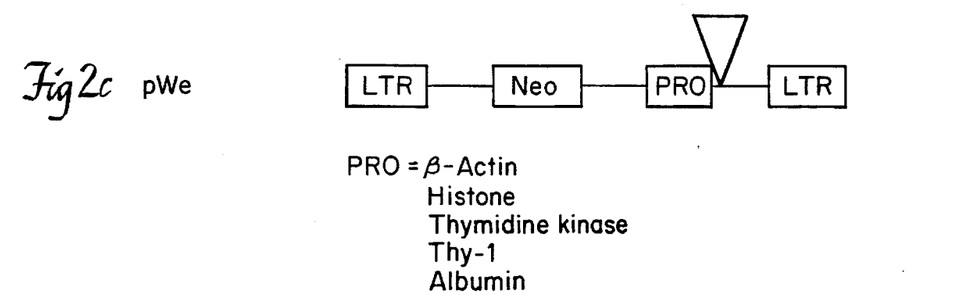
FIG. 2c is pWe.

[1] constructed, not tested for expression
[2] constructed, no expression when tested
[3] constructed, expression detected Vectors which include a selectable marker are represented in FIG. 2a, 2b and 2c. In FIG. 2a, pZIP neo SVX, described by Cepko is represented. Cepko, C. et al., *Cell*, 37:1053–1062 (1984). Here, there is a splice donor and splice acceptor, noted as SD and SA, between which the gene of interest is inserted, using known techniques. Expression of the inserted gene is based on the LTR in the unprocessed message; the processed message is responsible for expressing neomycin.

In FIG. 2b, vector pLJ is represented. In pLJ, the genetic material of interest is inserted just following the 5' LTR. Expression of this genetic material is transcribed from the LTR and expression of the neo gene is transcribed from an internal SV40 promoter.

In FIG. 2c, the pWe vectors are represented. In pWe vectors, the LTR promoter and transcript is responsible for expressing neomycin and an internal promoter is responsible for expression of the gene of interest. Promoters useful in this type of vector include promoters derived from chicken beta-actin, human histone, Herpes simplex thymidine kinase, thy 1 (a tissue-specific promoter used in T cells) and rat albumin.

Figure 2D:
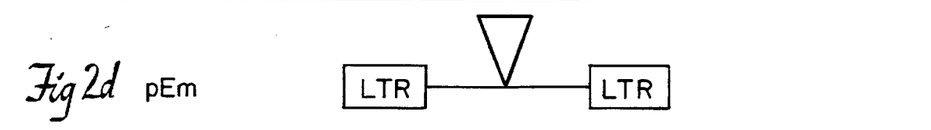
FIG. 2d is pEm.
Figure 2E:
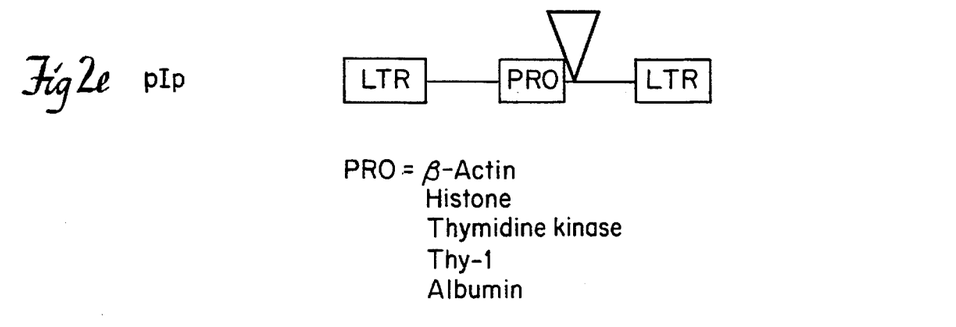
FIG. 2e is pip.
Figure 3:
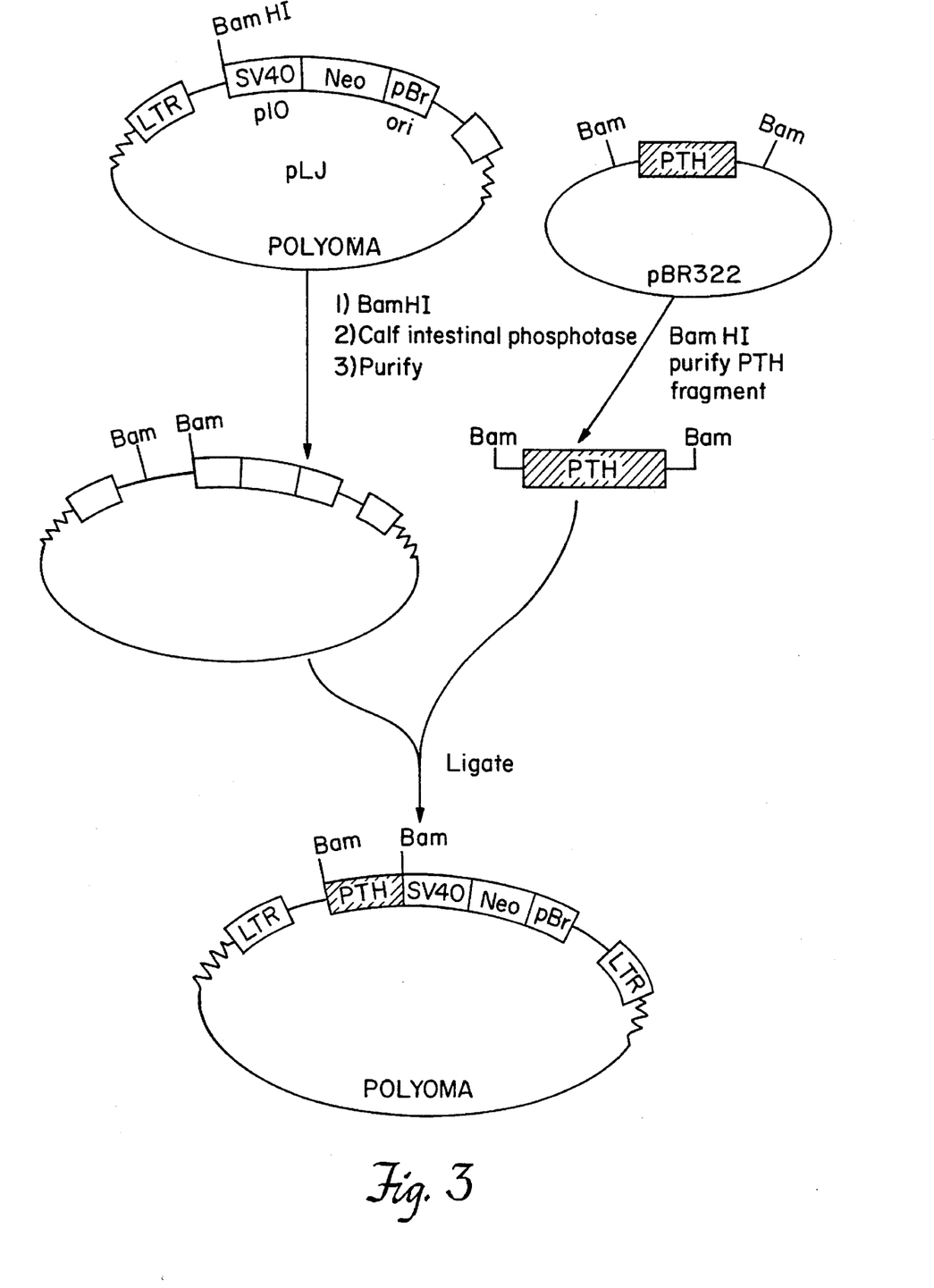
FIG. 3 is a schematic representation of the construction of a recombinant retroviral vector, using the pLJ vector represented in FIG. 2b and the human parathyroid hormone gene.

Vectors without a selectable marker can also be used to transduce fibroblasts with genetic material of interest. Such vectors are basically simplifications of the vectors previously described, in which there is such a marker. Vector pEm is represented in FIG. 2d; as represented, the main components of the vector are the 5' and 3' LTR, and the genetic material of interest, inserted between the two LTRs. pip represents a series of useful vectors in which there is an internal promoter. As represented in FIG. 2e, there is an LTR at each end, flanking an internal promoter; promoters useful in these vectors include those derived from chicken beta-actin, human histone, Herpes simplex thymidine kinase and rat thy 1.

Introduction of Genetic Material into Fibroblasts and Assessment of Expression of the Genetic Material A cell line which produces recombinant amphotropic retrovirus having a recombinant genome is used to infect fibroblasts. As described above, the recombinant genome can include a variety of components, but in general is comprised of two LTRs and, in place of the gag, the pol and the env sequences, a second promoter sequence and, in some cases, a gene encoding a selectable marker (e.g., neo).

Viral stocks, to be used in introducing genetic material of interest into fibroblasts, are harvested, as described above, supplemented with 8 micrograms per ml. (mcg/ml.) of Polybrene (Aldrich) and added to the culture of fibroblasts. If the titer of the virus is high (e.g., approximately $10^6$ cfu per ml.), then virtually all fibroblasts will be infected and no selection (e.g., of fibroblasts into which the vector, including the recombinant genome, has been introduced) is required. If the titer is very low, then it is necessary to use a retroviral vector that has a selectable marker, such as neo or his. If a selectable marker is used, after exposure to the virus, the cells are grown to confluence and split into selective media (e.g., media containing G418 if the selectable marker is neo, media containing histidinol and no histidine if the selectable marker is his).

The neo gene is a bacterial gene derived from the transposon Tn5, which encodes neomycin resistance in bacteria and resistance to the antibiotic G418 in mammalian cells. This neo gene acts as a dominant selectable marker; its presence in a mammalian cell converts the cell into one which will grow in the presence of G418. (If it is not present, the cell dies in the presence of G418.) As a result, the presence of this gene in a mammalian cell can be determined by culturing cells in media which contains G418. The recombinant retrovirus having this recombinant genome is referred to as the neo virus.

The recombinant retroviral vectors having the neo gene also have a cloning site. As a result, genetic material of interest can be introduced into the vector, incorporated into fibroblasts and expressed by fibroblasts transduced with the recombinant retrovirus (referred to as fibroblasts having incorporated genetic material).

At the BamHI cloning site, it is possible to insert genetic material of interest. The genetic material of interest can be DNA which does not normally occur in fibroblasts; DNA which normally occurs in fibroblasts but is not expressed by them at levels which are biologically effective (i.e., levels sufficient to produce the normal physiological effects of the polypeptide it encodes); DNA which occurs in fibroblasts and has been modified so that it is expressed by such cells; and any DNA which can be modified to be expressed by fibroblasts, alone or in any combination thereof.

A copy of the gene encoding human parathyroid hormone (hPTH) has been cloned into this site, (e.g., into pLJ) in the following way: The pLJ plasmid was digested with BamHI and subsequently treated with the enzyme calf intestinal phosphatase. Following this, the linear vector was fractionated on agarose gel and purified, using glass beads. In addition, the BamHI fragment containing the human PTH gene was prepared from the plasmid described by Hendy et al., which contains a complete cDNA of human PTH cloned into pBR322. Hendy, G.N. et al., *Proceedings of the National Academy of Sciences*, USA, 78:7365–7369 (1981).

A sub fragment of the PTH cDNA, containing 17 bp of 5' untranslated, all coding and 31 bp of 3' untranslated sequence, was isolated by digesting the initial plasmid with DdeI and HinfI and isolating the 600bp fragment. The ends of this fragment were treated with DNA polymerase, to fill in the recessed ends. BamHI linkers were ligated to the blunt ends with $T_4$ DNA ligase. An authentic BamHI restriction fragment was generated by digesting the ligation mixture from above with BamHI. This was then subcloned into the BamHI site of pBR322, which is the plasmid used as the source of hPTH in vector construction.

Equal quantities of the pLg linear backbone and the BamHI PTH fragment were added together, in the presence of T4 DNA ligase. The resulting mixture was maintained under conditions appropriate for ligation of the two fragments. The ligation mixture was used to transform bacteria HB101, which were then plated onto agar containing Kanamycin. Maniatis, T. et al., *Molecular Cloning: A Laboratory Manual*, Cold Spring Harbor Laboratory, p.p. 250–251, 504; Bolivar, F. and K. Backman, *In: Methods in Enzymology*, R. Wu (ed.), Vol. 68, Academic Press, N.Y. (1979). The resulting colonies were analyzed for the recombinant plasmid.

Parathyroid hormone is a polypeptide which has a role in the regulation of calcium in the body. Although the hPTH gene is present in human fibroblasts, it is not expressed in those cells at biologically significant levels. Fibroblasts capable of making a polypeptide hormone such as hPTH, or another substance not normally made by such cells at biologically significant levels, can be engrafted onto an individual and serve as a continuous supply system for the hormone, or other substance.

This process is described with reference to hPTH, but it is to be understood that any gene can be introduced into fibroblasts, using the method described, and its expression by the cells can be assessed in a similar manner. As explained, DNA encoding the proteins or functions listed in Table 1 has been cloned into retroviral vectors and in many cases, introduced into fibroblasts in a similar manner and expressed by the transduced cells.

The Psi am cells producing the recombinant virus construct which contained the hPTH-encoding DNA and DNA encoding a selectable marker (such as the neo gene), were used to produce a viral stock, as described above. The viral stock was harvested; fibroblasts to be transduced with the virus containing the hPTH gene were incubated with the stock. In this case, a selectable marker is used to identify and select for transduced fibroblasts by culturing on media containing G418. If the viral titer is sufficiently high, that essentially all fibroblasts are infected and selection, using a selectable marker and appropriate media, is not needed.

Diploid fibroblasts from a Wistar rat transduced with DNA encoding hPTH according to the method of the present invention have been deposited at the American Type Culture Collection (Rockville, MD) under deposit number CRL9514. The ability of fibroblasts transduced with the recombinant retrovirus having the hPTH gene to express the hPTH gene has been assessed, both in vitro and in vivo.

In vitro assessment was carried out as follows:

The in vitro production of hPTH by NIH 3T3 cells infected with a virus containing the hPTH gene and selected in neomycin and by secondary cultures of fibroblasts established from a Wistar rat (FWR) was assessed. NIH 3T3 cells are cells derived from a mouse embryo and immortalized by selective cultivation in vitro. The FWR cells were derived from an explant from a syngeneic strain of rats (Wistar). The cells have a limited life span and are referred to as secondary cultures.

Both types of cells had previously been infected with virus and selected in neomycin, as described above. After selection, each type of cell was seeded onto 10 cm tissue culture dishes and grown to confluence. Fresh culture media (DME with 10% CS and penicillin and streptomycin) was then added; this point is referred to subsequently as time zero. At subsequent times, aliquots of media were harvested and frozen. At the end of 24 hours all media was removed from the cell and placed back in the incubator; 12 hours later an additional aliquot was taken for analysis of the lability of the human PTH in tissue culture.

Figure 4:
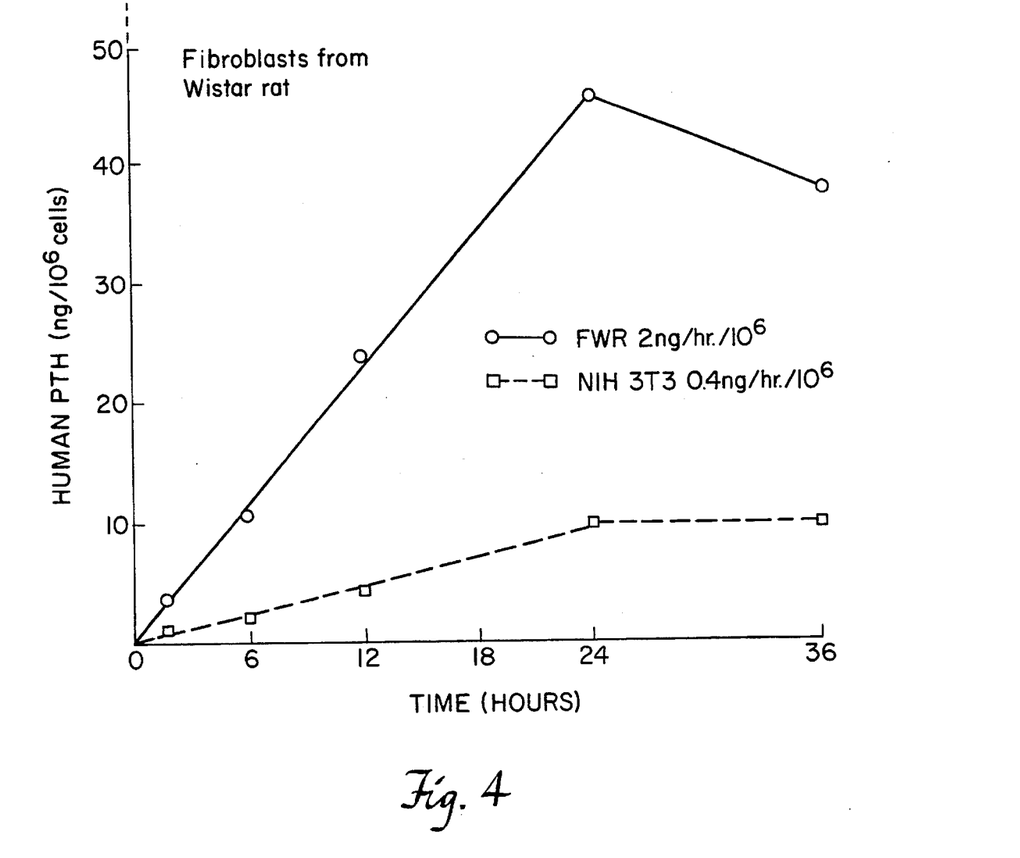
FIG. 4 is a graph representing the quantity of human parathyroid hormone produced, in the designated time period, by transduced fibroblasts. The dashed line represents production by transduced NIH 3T3 cells on tissue culture plates. The solid line represents production by transduced fibroblasts derived from a rat and grown on tissue culture plates.

The aliquots were analyzed for the presence of hPTH using a radioimmunoassay (Nichols) which measures intact hPTH. The technique is described in Allegro™ Intact PTH/Immunoassay System for the Quantitative Determination of Human Intact Parathyroid Hormone in Serum, Nichols Institute Diagnostics, San Juan Capistrano, CA (36B-2170, Effective 7/86 Revised), the teachings of which are incorporated herein by reference. The assay has a sensitivity of approximately one nanogram/milliliter serum (ng/ml) and was shown to be specific for human PTH in that it does not cross react with rat PTH. The results of the experiments are plotted as the production of hPTH, as measured by RIA, over time. Results are shown in FIG. 4.

The same analysis was also carried out after the Wistar rat fibroblasts which had been infected and selected were seeded onto Cytodex beads. When the cells were subconfluent on the beads, fresh media was added; aliquots were taken and the production rate of PTH was measured. Under these conditions, the rate of production was twice that as measured in tissue culture on tissue culture plastic. In both cases, at the end of the assessment period, cells were harvested by trypsinization and counted. In vivo assessment was conducted as follows:

Approximately $2 \times 10^7$ engineered fibroblasts were injected into the intraperitoneal cavity of syngeneic rats, either alone or after having been grown to confluence on cytodex 3 microcarrier beads. Rats into which only phosphate buffer saline (PBS) or beads alone, in similar quantities, were injected intraperitoneally served as controls. A control rat received an injection intraperitoneally (IP) of PBS alone. A second control animal received an injection IP of $2 \times 10^7$ FWR cells expressing human PTH; they were administered in suspension in PBS. Another control rat received 300 mg of Cytodex 3 beads alone (i.e., without any cells). A fourth rat received approximately 150 mg of Cytodex 3 beads coated with FWR PTH cells, corresponding to approximately $2 \times 10^7$ cells. A fifth rat was administered approximately 200 mg of beads coated with FWR fibroblasts (approximately $2-3 \times 10^7$ cells). The time of injection is referred to as T=0.

Engraftment of the transduced fibroblasts was verified by determining the presence of hPTH in recipient's blood, using a radioimmunoassay specific for hPTH. hPTH was detected in serum over a 3-week post-transplantation period.

In all animals, the first measurement was obtained at T=3 hours (3 hours after injection). This was done by obtaining approximately ½ ml. of blood through the tail vein of each of the animals. Blood was then allowed to clot and the serum was analyzed for hPTH through the use of the Nichols radioimmunoassay described above. This was repeated; at various times approximately ½ ml. of blood was obtained, through rat tail phlebotomy, and analyzed for hPTH. Results of these determinations are shown in the table. Also shown in the table are results of serum calcium levels in these animals.

TABLE 2

| | \multicolumn{10}{c}{Assessment of in vivo expression of human PTH} |
| TIME (DAYS) | RAT #1 | | RAT #2[a] | | RAT #3[b] | | RAT #4c | | RAT #5[c] | |
| | Ca (mg/%) | HPTH (pg/ml.) | Ca (mg/%) | HPTH (pg/ml.) | Ca (Mg/%) | HPTH (pg/ml.) | Ca (mg/%) | HPTH (pg/ml.) | Ca (mg/%) | HPTH (pg/ml.) |
|---|---|---|---|---|---|---|---|---|---|---|
| −3 | — | | — | | 10.70 | 1.5 | | | | |
| −2 | — | | — | | 9.0 | 1 | 10.62 | 1 | 10.47 | 1 |
| −1 | — | | — | | 9.13 | 1 | 10.14 | 1 | 9.81 | 1 |
| 0 | 9.73 | 1 | 9.96 | 1 | 10.11 | 1 | 10.99 | 1 | — | — |
| 3 hr. | 8.48 | 1 | 7.54 | 55 | 10.13 | 1 | 9.22 | 170 | 9.99 | 120 |
| 1 | — | — | 8.81 | — | 9.29 | 1 | 9.47 | 1 | 9.79 | 30 |
| 2 | 10.69 | 1 | 10.66 | 1 | 10.18 | 1 | 10.58 | 1 | 10.35 | 1 |
| 3 | 9.89 | 1 | 10.10 | 1 | 9.90 | 1 | 9.97 | 1 | 10.44 | 1 |
| 4 | 10.29 | 1 | 9.51 | 1 | 9.62 | 1 | 9.33 | 1 | 9.49 | 21 |
| 5 | 9.68 | 1 | 9.92 | 1 | 8.28 | 1 | 9.83 | 1 | 9.73 | 39 |
| 6 | 0.04 | 1 | 9.82 | 1 | — | — | | | | |
| 7 | 9.61 | 1 | 9.75 | 1 | 9.82 | 1 | 9.7 | 1 | 9.1 | 1 |
| 8 | 10.1 | 1 | 9.74 | 1 | 10.2 | 1 | 10.22 | 1 | 10.6 | 1 |
| 9 | 9.02 | 1 | 8.66 | 1 | — | — | — | | — | |
| 10 | 8.70 | 1 | 8.68 | 1 | — | | — | | | |
| 19 | — | | — | | 9.46 | 1 | 9.61 | 35 | 9.64 | 40 |
| 20 | — | | — | | — | | | 1 | | |
| | | | | | | | | | —1 | |

Figure 5:
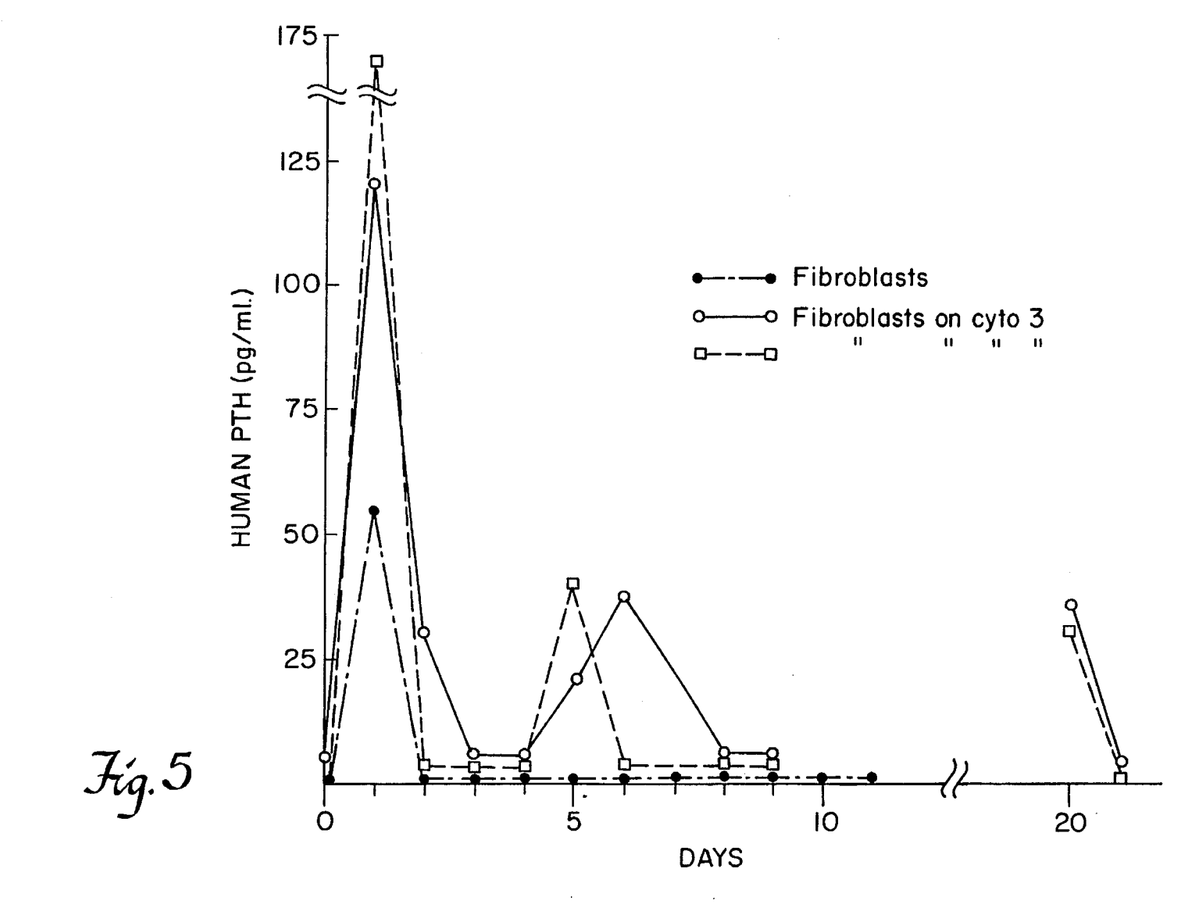
FIG. 5 is a graph representing the quantity of human parathyroid hormone produced, in the designated time periods, in rats injected with either transduced fibroblasts alone (blackened circles) or transduced fibroblasts coated onto cyto 3 beads and grown to confluence.

[a]Injected with free PTH-fibroblasts (IP)
[b]Injected with beads?
[c]Injected with PTH fibro-beads (Cytodex 2 or 3) T = = time of injection Results of this assessment are represented in FIG. 5. Within 3 hours after injection of transduced fibroblasts alone, 60 picograms (pg.) hPTH were detected per milliliter (ml.) of recipient's serum. (Normal human serum PTH levels range from 10—50 pg/ml.) Within 3 hours after injection of transduced fibroblasts confluent on beads, hPTH levels of 120 pg/ml. or 175 pg/ml. serum were detected. As is also shown in the table, rats injected with transduced fibroblasts containing the hPTH gene did not become hypercalcemic. This is unexpected because experiments in vitro suggest hPTH is active in rat tissue. One possible explanation is that counter regulatory mechanisms were activated (i.e., calcitonin).

As a result, it has been demonstrated that transduced fibroblasts secrete a polypeptide hormone which is normally not secreted at biologically significant levels by fibroblasts and, additionally, that they can secrete this hormone at physiological (or greater) concentrations. Transplantation of the fibroblasts secreting human parathyroid hormone (here, into the intraperitoneal cavity) demonstrated that the phenotypic change conferred on the fibroblasts by the retrovirus (i.e., secretion of hPTH) is detected systemically in the recipient. Administration of transduced fibroblasts, in a similar manner, to parathyroidectomized rats can further demonstrate the effectiveness of hPTH produced.

Thus, in one embodiment of the method of the present invention, fibroblasts are transduced, using a retroviral vector in which the recombinant genome includes DNA of interest and, optionally, DNA encoding a dominant selectable marker. Transduced cells are isolated and grown to sufficient numbers. They are introduced into a recipient by transplantation (e.g., into the intraperitoneal cavity, into the central nervous system). Alternatively, fibroblasts are similarly transduced, isolated, grown and then transplanted in conjunction with or bound to a matrix. This approach is particularly useful when long-term (several weeks or longer) engraftment is desired. The matrix used can be, as described, a support such as microcarrier beads, particularly collagen-coated microcarrier beads. The matrix can be virtually any solid matrix of suitable size. A skin graft, which contains transduced fibroblasts, can be applied.

Introduction of Genetic Material Encoding Polypeptides Other Than hPTH

Genes encoding polypeptides other than hPTH can also be introduced into fibroblasts by means of the retroviral vector. For example, a gene encoding human growth hormone (HGH) or a gene encoding insulin can be introduced into fibroblasts. Such genes can be introduced into fibroblasts, alone or in combination with a gene encoding a selectable marker, such as the neo gene. HGH is a polypeptide of about 29,000 Daltons which is normally secreted only by the hypothalamus. Insulin is a polypeptide which regulates glucose levels in the bloodstream.

These genes, as well as others (e.g., some of those listed above), have been introduced into fibroblasts in the same manner as described above for the hPTH gene and the resulting transduced fibroblasts can be grafted onto an appropriate site on the body.

Use of Other Dominant Selectable Markers in the Introduction of Genetic Material Encoding Polypeptides It is also possible to use dominant selectable markers other than the neo gene to introduce genetic material into fibroblasts. For example, the His D gene can be used for this purpose. The His D gene is a bacterial gene from Salmonella and encodes histidinol dehydrogenase, a polypeptide which converts histidinol to histidine. Histidine is an essential amino acid; histidinol is an alcohol analogue of histidine and can be converted to histidine under the proper metabolic conditions. If cells are grown in media containing histidinol but lacking histidine, those cells having the His D gene can convert histidinol to histidine. Because histidine is essential to their function, those cells which have the His D gene (and thus can make histidine) will survive and those lacking the gene will not.

A retrovirus vector having the His D gene has been used to infect keratinocytes. The keratinocytes containing His D gene were selected by growing these cells in media lacking histidine but containing histidinol. As expected, keratinocytes having the His D gene formed colonies and grew to confluence; those lacking the gene did not. In fact, such cells occurred at a much higher frequency than those in which the neo gene was included. These same techniques are useful in selecting fibroblasts containing DNA of interest.

As a result of this work, it is also possible to use independent dominant selectable markers (e.g., the neo gene and the His D gene) to introduce new genetic material into fibroblasts. In the case of polypeptides which have two different subunits, for example, separate dominant selectable markers can be used to introduce the genetic information encoding the two subunits. In addition, two or more dominant selectable markers can be used in the case of polypeptides which need to be specifically cleaved or processed in order to become active (e.g., insulin and parathyroid hormone). A gene encoding the necessary processing enzyme can be introduced along with the gene encoding the polypeptide hormone requiring such processing. This would enable fibroblasts to process that polypeptide hormone.

Other Vehicles for the Introduction of Genetic Material of Interest into Fibroblasts It is also possible to use vehicles other than retroviruses to genetically engineer or modify fibroblasts. Genetic information of interest can be introduced into fibroblasts by means of any virus which can express the new genetic material in such cells. For example, SV40, herpes virus, adenovirus and human papilloma virus can be used for this purpose.

Introduction of Genetic Material of Interest into Other Types of Cells

Using the method of the present invention, it is also possible to incorporate genetic material of interest into other types of cells. The method can be used to introduce genetic material of interest into any system in which cells can be harvested from tissue, grown in tissue culture on a solid matrix and infected with a retrovirus. Genetic material of interest can also be incorporated into the central nervous system. For example, it can be introduced into fibroblasts or into glial cells, or neuroglial cells, which are non-neuronal cellular elements of the central and the peripheral nervous systems. The transduced cells can be introduced into the recipient animal. This can be done through stereotactic administration, directly into specific areas of the brain, or by being introduced into the cerebrospinal fluid. In the central nervous system, glial cells include oligodendroglia cells, astrocytes, ependymal cells and microglia cells. In the peripheral nervous system, they include the satellite cells of ganglia and the neurolemmal (or Schwann) cells around peripheral nerve fibers.

Genetic material of interest, such as the purine salvage enzyme hypoxanthine guanine phosphoribosyl transferase (HPRT) can be introduced into glial cells for the purpose of correcting the inherited deficiency of HPRT which results in the Lesch-Nyhan Syndrome; a devastating genetic disease with numerous CNS abnormalities. It can also be introduced into the central nervous system to treat or prevent, for example, degenerative diseases (e.g., by introducing genetic material encoding nerve growth factor), Parkinson's Disease (e.g., by introducing genetic material encoding DOPA synthetic enzymes) and genetic disorders caused by an "abnormal" gene (e.g., Huntington's Disease, manic depression, Alzheimer's Disease), in which the abnormal gene can be replaced, its function corrected or counteracted, or production of an encoded product altered.

Genetic material of interest can also be introduced into endothelial cells, which cover the serous membranes and line the heart, blood vessels, lymphatics and the anterior chamber of the eye. Genetic material of interest, such as hPTH, can be introduced into such cells in order to facilitate its delivery into the bloodstream.

Uses of Fibroblasts and Other Cells Having Incorporated Genetic Material

The present invention makes it possible to genetically engineer fibroblasts in such a manner that they produce polypeptides and proteins not normally produced in fibroblasts in biologically significant amounts and secrete them into the bloodstream or other area of the body, such as the central nervous system. The fibroblasts formed in this way can serve as a continuous drug delivery system to replace present regimens, which require periodic administration (by ingestion, injection, etc.) of the needed substance.

For example, it can be used to provide continuous delivery of insulin, which at the present time, must be isolated from the pancreas, extensively purified and then injected into the body by those whose insulin production or utilization is impaired. In this way, insulin can be introduced into the body via a continuous drug delivery system and, as a result, there would be no need for daily injections of insulin.

Genetically engineered fibroblasts can also be used for the production of clotting factors. Hemophiliacs lack a protein called Factor VIII, which is involved in clotting. Factor VIII is now administered by injection. Fibroblasts having genes encoding Factor VIII, can be used to make a skin graft in which they produce Factor VIII; as a skin graft, the tissue would secrete the factor into the bloodstream.

Incorporation of genetic material of interest into fibroblasts and other types of cells would be particularly valuable in the treatment of inherited disease and the treatment of acquired disease. In the case of inherited diseases, this approach is used to provide genetically modified fibroblasts and other cells which can be used as a metabolic sink. That is, such fibroblasts would serve to degrade a potentially toxic substance. For example, this could be used in treating urea cycle disorders. Fibroblasts of the present invention can also be used in the treatment of genetic diseases in which a product (e.g., an enzyme or hormone) normally produced by the body is not produced or is made in insufficient quantities. Here, fibroblasts transduced with a gene encoding the missing or inadequately produced substance can be used to produce it in sufficient quantities. For example, this can be used in producing alpha-1 anitrypsin. It can also be used in the production of Factor VIII and Factor IX and thus would be useful in treating hemophilia.

There are many acquired diseases for which treatment can be provided through use of genetically engineered fibroblasts (i.e., fibroblasts transduced with genetic material of interest). For example, such cells can be used in treating anemia, which is commonly present in chronic disease and often associated with chronic renal failure (e.g., in hemodialysis patients). In this case, fibroblasts having incorporated in them a gene encoding erythropoietin would correct the anemia by stimulating the bone marrow to increase erythropoiesis (i.e. production of red blood cells).

Fibroblasts of the present invention can also be used to administer a low dose of tissue plasminogen activator as an activator to prevent the formation of thrombi. In this case, fibroblasts having incorporated genetic material which encodes TPA would be transplanted into an individual in whom thrombus prevention is desired. This would be useful, for example, as a prophylactic against common disorders such as coronary artery disease, cerebrovascular disease, peripheral vascular occlusive disease, vein (e.g., superficial) thrombosis, such as seen in pulmonary emboli, or deep vein thrombosis. Fibroblasts which contain DNA encoding calcitonin can be used in the treatment of Paget's Disease, a progressive, chronic disorder of bone metabolism, in which calcitonin is presently administered subcutaneously.

Another application for a skin graft having genetically engineered fibroblasts is in birth control. Tests are underway now for using a polypeptide hormone called lutenizing hormone releasing hormone (LHRH) in regulating fertility. Continuous administration of LHRH results in a sterile individual; when administration ceases, the individual is again fertile. Rather than taking LHRH injections or oral medication, one could have a small graft which continuously secretes LHRH to provide the same effect. In the event that the person wanted to regain fertility this transplant could be excised; delivery of the polypeptide hormone would cease.

Fibroblasts engineered to produce and secrete interleukins (e.g., IL-1, IL-2, IL-3) can be used in several contexts. For example, the result of some of the therapies now used (e.g., chemotherapy) is induction of neutropenia (the presence of abnormally low numbers of neutrophils in the blood), often caused by direct suppression of the bone marrow. For example, use of virtually all the chemotherapeutic agents, as well as AZT, used in the treatment of (AIDS) Acquired Immune Deficiency Syndrome, results in neutropenia. This condition results in numerous life-threatening infections. In these cases, administration of, for example, IL-3 through transplantation of fibroblasts which contain genetic material encoding IL-3 can be used to increase the neutrophil count. In addition, the administration of thrombopoietin, which stimulates the production of platelets, can be used in the treatment of numerous conditions in which platelet count is low. In this case, fibroblasts transduced with the gene for thrombopoietin can be applied to an individual; production and secretion of the encoded product will result in stimulation of platelet production.

Another related application of fibroblasts having incorporated genetic material is in the treatment of AIDS. Interleukin 2 and Interleukin 3, which stimulate the immune system, are potentially valuable in the treatment of AIDS. They could be delivered by a skin graft having fibroblasts which have been genetically engineered to produce these two polypeptides (which are now administered by periodic injection).

Another use of the present invention is in the treatment of enzyme defect diseases. In this case the product (polypeptide) encoded by the gene introduced into fibroblasts is not secreted (as are hormones); rather, it is an enzyme which remains inside the cell. There are numerous cases of genetic diseases in which an individual lacks a particular enzyme and is not able to metabolize various amino acids or other metabolites. The correct genes for these enzymes could be introduced into a skin transplant; the transplant would then carry out that metabolic function. For example, there is a genetic disease in which those affected lack the enzyme adenosine deaminase. This enzyme is involved in the degradation of purines to uric acid. It might be possible, using the present invention, to produce a skin graft capable of producing the missing enzyme at sufficiently high levels to detoxify the blood as it passes through the area to which the graft is applied.

The present invention also has veterinary applications. It can be used, for example, in delivering substances such as drugs (e.g., antibiotics) and hormones to animals, which would otherwise be provided by being incorporated into their feed, added to their water or injected periodically (e.g., daily or less frequently). Use of the modified fibroblasts of the present invention has the advantage that the tissue formed of the modified cells can be applied to the animal and will provide quantities of the encoded protein on an ongoing basis, thus eliminating the need for daily/periodic administration of the substance.

Industrial Utility

This invention has industrial applicability in providing hormones, enzymes and drugs to mammals, including humans, in need of such substances. For example, it can be used to provide a continuous supply of a hormone which otherwise would be administered on a intravenously, intramuscularly or subcutaneously. It is particularly valuable in providing such substances, such as hormones (e.g., parathyroid hormone, insulin), which are needed for extended periods of time.

Equivalents

Those skilled in the art will recognize, or be able to ascertain using no more than routine experimentation, many equivalents to the specific embodiments of the invention described specifically herein. Such equivalents are intended to be encompassed in the scope of the following claims.

We claim:

1. Fibroblasts transduced by a recombinant retrovirus comprising incorporated genetic material, said transduced fibroblasts bound to a supporting matrix in vitro and having the property of being capable of expressing said incorporated genetic material in vivo.

2. Fibroblasts according to claim 1, wherein said incorporated genetic material encodes a polypeptide or protein.

3. Fibroblasts according to claim 1, wherein said incorporated genetic material comprises at least one gene encoding a selectable marker.

4. Fibroblasts according to claim 3, wherein said gene encoding a selectable marker encodes neomycin resistance.

5. Fibroblasts according to claim 1, wherein:

(a) the genome of said recombinant retrovirus further comprises long terminal repeat sequences, a tRNA binding site, and a Psi packaging site derived from amphotropic Moloney murine leukemia virus; and (b) said recombinant retrovirus is amphotropic.

6. Fibroblasts according to claim 3, wherein:

(a) the genome of said recombinant retrovirus further comprises long terminal repeat sequences, a tRNA binding site, and a Psi packaging site derived from amphotropic Moloney murine leukemia virus; and (b) said recombinant retrovirus is amphotropic.

7. Fibroblasts according to claim 1, wherein the genome of said recombinant retrovirus further comprises a regulatable eukaryotic promoter.

8. Fibroblasts according to claim 3, wherein the genome of said recombinant retrovirus further comprises a regulatable eukaryotic promoter.

9. Fibroblasts according to claim 1, wherein said recombinant retrovirus is selected from the group consisting of pRO, pEM, and pIP.

10. Fibroblasts according to claim 3, wherein said recombinant retrovirus is selected from the group consisting of pRO, pEM, and pIP.

11. Fibroblasts according to any one of claims 1, 2, 3, 4, 5, 6, 7, 8, 9 or 10, wherein said supporting matrix comprises microcarrier beads.

12. A method of making transduced fibroblasts having the property of being capable of expressing incorporated genetic material in vivo, comprising the steps of:

(a) binding fibroblasts to a supporting matrix; and (b) contacting said bound fibroblasts with a recombinant retrovirus comprising incorporated genetic material under conditions appropriate for retroviral infection.

13. The method of claim 12, wherein said incorporated genetic material encodes a polypeptide or protein.

14. The method of claim 12, wherein said incorporated genetic material comprises at least one gene encoding a selectable marker.

15. The method of claim 12, further comprising the step of culturing said fibroblasts under suitable growth conditions.

16. The method of claim 14, further comprising the step of culturing said fibroblasts under suitable growth conditions.

17. The method according to any one of claims 12, 13, 14, 15, or 16, wherein said supporting matrix comprises microcarrier beads.

* * * * *